(12) United States Patent
White et al.

(10) Patent No.: US 9,482,595 B2
(45) Date of Patent: Nov. 1, 2016

(54) ROTOR STATE SENSOR SYSTEM

(71) Applicant: Sikorsky Aircraft Corporation, Stratford, CT (US)

(72) Inventors: Matthew A. White, Milford, CT (US); Patrick J. Dempsey, New Haven, CT (US); Aaron Kellner, Bloomfield, CT (US); Joshua King, Hamden, CT (US)

(73) Assignee: SIKORSKY AIRCRAFT CORPORATION, Stratford, CT (US)

( * ) Notice: Subject to any disclaimer, the term of this patent is extended or adjusted under 35 U.S.C. 154(b) by 212 days.

(21) Appl. No.: 14/173,374

(22) Filed: Feb. 5, 2014

(65) Prior Publication Data

US 2015/0219523 A1 Aug. 6, 2015

(51) Int. Cl.
*G01M 13/00* (2006.01)
*B64C 27/57* (2006.01)
*G01M 17/00* (2006.01)
*G01N 21/55* (2014.01)

(52) U.S. Cl.
CPC .............. *G01M 13/00* (2013.01); *B64C 27/57* (2013.01); *G01M 17/00* (2013.01); *G01N 21/55* (2013.01)

(58) Field of Classification Search
CPC ...... B64C 27/008; B64C 27/54; G01B 11/16
See application file for complete search history.

(56) References Cited

U.S. PATENT DOCUMENTS

| | | | |
|---|---|---|---|
| 3,957,227 A * | 5/1976 | Baskin | 244/17.25 |
| 4,095,477 A | 6/1978 | Morris et al. | |
| 4,583,862 A * | 4/1986 | Ferrar et al. | 356/139.03 |
| 4,721,386 A | 1/1988 | Collyer | |
| 4,812,643 A * | 3/1989 | Talbot | 250/222.1 |
| 5,552,883 A * | 9/1996 | Busch-Vishniac et al. | 356/139.03 |
| 6,422,816 B1 | 7/2002 | Danielson | |
| 6,693,548 B2 | 2/2004 | Boyce et al. | |
| 6,811,376 B2 | 11/2004 | Arel et al. | |
| 6,932,569 B2 | 8/2005 | Torok et al. | |
| 7,105,765 B2 | 9/2006 | Child | |
| 7,227,627 B1 | 6/2007 | Bussard | |
| 7,332,884 B2 | 2/2008 | Rozman et al. | |
| 7,403,294 B2 * | 7/2008 | Handman et al. | 356/601 |
| 7,567,047 B2 | 7/2009 | Rozman | |

(Continued)

FOREIGN PATENT DOCUMENTS

JP 2010149602 A 7/2010

OTHER PUBLICATIONS

Eureopean Search Report issued in EP Application No. 14196097.1-1754, Jun. 15, 2015, 9 pages.

*Primary Examiner* — Khoi Tran
*Assistant Examiner* — Ryan Rink
(74) *Attorney, Agent, or Firm* — Cantor Colburn LLP

(57) ABSTRACT

A rotor state sensor system is provided for use with a rotor including a hub, a hub arm and a blade coupled to the hub by the hub arm. The sensor system includes sensors disposed on the hub arm to define a first plane, which emit emissions and receive reflected emissions, and which generate a signal according to the received reflected emissions, reflector plates disposed on the blade which define a second plane at locations where the emissions from the sensors are incident on the reflector plates and from which the reflected emissions are reflected towards the sensors and a computing device which receives the signal from the sensors, determines relative orientations of the first and second planes according to the received signal and determines a condition of the rotor based on the determined relative orientations.

9 Claims, 5 Drawing Sheets

(56) References Cited

U.S. PATENT DOCUMENTS

| | | |
|---|---|---|
| 7,824,147 B2 | 11/2010 | Morris et al. |
| 8,339,010 B2 | 12/2012 | Atarashi et al. |
| 2007/0132461 A1 | 6/2007 | Holmquist et al. |
| 2009/0321555 A1 | 12/2009 | Nitzsche et al. |
| 2011/0191040 A1* | 8/2011 | Bechhoefer et al. .......... 702/56 |
| 2012/0068005 A1 | 3/2012 | Kessler et al. |
| 2012/0078544 A1 | 3/2012 | Lynch |
| 2013/0243597 A1 | 9/2013 | Perrin |
| 2013/0304400 A1 | 11/2013 | Isom |
| 2014/0271188 A1* | 9/2014 | Dillon ............................. 416/1 |
| 2014/0277855 A1* | 9/2014 | Sahasrabudhe et al. ......... 701/3 |

* cited by examiner

ROTOR STATE SENSOR SYSTEM

FEDERAL RESEARCH STATEMENT

This invention was made with government support under contract no. W911W6-10-2-0004 awarded by the Department of the Army. The government has certain rights to the invention.

BACKGROUND OF THE INVENTION

The subject matter disclosed herein relates to a rotor state sensor system and, more particularly, to a three point displacement rotor state system.

Fly-by-wire (FBW) control systems provide for helicopter stability, response predictability and maneuvering agility while allowing pilots to effectively manage mission and situational awareness. Modern vehicle management systems (VMS) are becoming highly integrated and comprehensive, which effectively protects the aircraft from vibration, provides condition based maintenance, improves maneuvering capability and adapts to mission and environmental demands. At the same time, a unique and critical system on a helicopter is the rotor system, which is highly complex and consists of numerous moving parts. It would be beneficial for the vehicle control and management systems noted above to utilize rotor information, although current production rotors have few (if any) flight control or sensors in the rotating frame.

The rarity of rotors with sensors in the rotating frame can be attributed to many factors including, but not limited to, input/output (I/O) processing increases, increased numbers of sensors in total and increased redundancy requirements. Additional factors can include the fact that the rotor environment can be harsh for sensor equipment, the fact that the available sensors may have low quality and high costs and the fact that it can be difficult to transmit sensor data from the rotating frame to the non-rotating frame.

BRIEF DESCRIPTION OF THE INVENTION

According to one aspect of the invention, a rotor state sensor system is provided for use with a rotor including a hub, a hub arm and a blade coupled to the hub by the hub arm. The sensor system includes sensors disposed on the hub arm to define a first plane, which emit emissions and receive reflected emissions, and which generate a signal according to the received reflected emissions, reflector plates disposed on the blade which define a second plane at locations where the emissions from the sensors are incident on the reflector plates and from which the reflected emissions are reflected towards the sensors and a computing device which receives the signal from the sensors, determines relative orientations of the first and second planes according to the received signal and determines a condition of the rotor based on the determined relative orientations.

In accordance with further embodiments, the rotor state sensor system further includes a transmission system by which signals are transmittable between the sensors and the flight computer.

In accordance with further embodiments, the reflector plates are disposed on a radially inward portion of the blade.

In accordance with further embodiments, the condition includes at least one or more of a lead/lag condition and a flapping condition.

In accordance with further embodiments, a helicopter is provided and includes a non-rotating frame in which the computing device is disposed and a rotating frame comprising the rotor, the sensors and the reflector plates, wherein the computing device is further configured to adjust commanded pitch angles in accordance with the signals.

According to another aspect of the invention, a rotor state sensor system is provided and includes a rotor including a hub, a hub arm and a blade coupled to the hub by the hub arm, sensors disposed on the hub arm to define a first plane, reflector plates disposed on the blade such that emissions generated by the sensors define a second plane at locations where the emissions are incident on the reflector plates and a computing device receptive of first and second signals from the sensors, the first and second signals being indicative of relative orientations of the first and second planes with respect to one another. The computing device is configured to determine at least one or more of a lead/lag condition and a flapping of the rotor based on the signals.

In accordance with further embodiments, the rotor state sensor system further includes a transmission system by which the first and second signals are transmittable between the sensors and the flight computer.

In accordance with further embodiments, the reflector plates are disposed on a radially inward portion of the blade.

In accordance with further embodiments, a helicopter is provided and includes a non-rotating frame in which the computing device is disposed and a rotating frame comprising the rotor, the sensors and the reflector plates, wherein the computing device is further configured to adjust commanded pitch angles in accordance with the signals.

According to yet another aspect of the invention, a method of operating a helicopter is provided and includes receiving pilot commands, converting the received pilot commands into commanded pitch angles for a blade of a rotor, determining whether the commanded pitch angles and actual pitch angles are in line with one another and adjusting the commanded pitch angles in an event the actual pitch angles are different from the commanded pitch angles.

In accordance with further embodiments, the determining comprises determining relative orientations between a first plane associated with a hub arm of the rotor and a second plane associated with the blade.

These and other advantages and features will become more apparent from the following description taken in conjunction with the drawings.

BRIEF DESCRIPTION OF THE DRAWINGS

The subject matter, which is regarded as the invention, is particularly pointed out and distinctly claimed in the claims at the conclusion of the specification. The foregoing and other features, and advantages of the invention are apparent from the following detailed description taken in conjunction with the accompanying drawings in which:

The detailed description explains embodiments of the invention, together with advantages and features, by way of example with reference to the drawings.

DETAILED DESCRIPTION OF THE INVENTION

As will be described below, a rotor state sensor system is provided and serves to measure blade motion or blade position during flight. The system can be employed in order to improve performances of control and management systems, to reduce loads and to monitor blade health.

Figure 1:
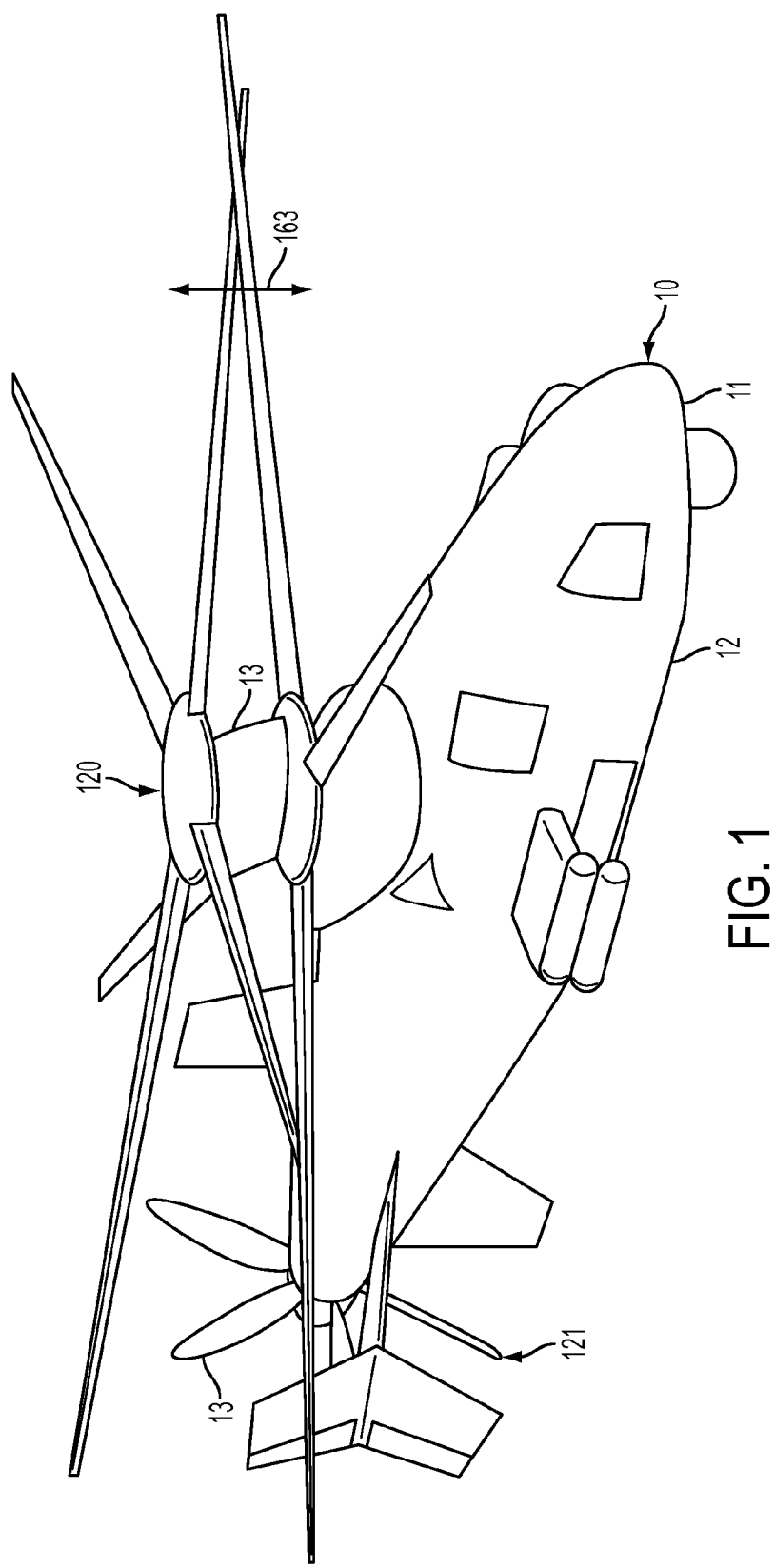
FIG. 1 is a perspective view of an aircraft in accordance with embodiments.
Figure 2:
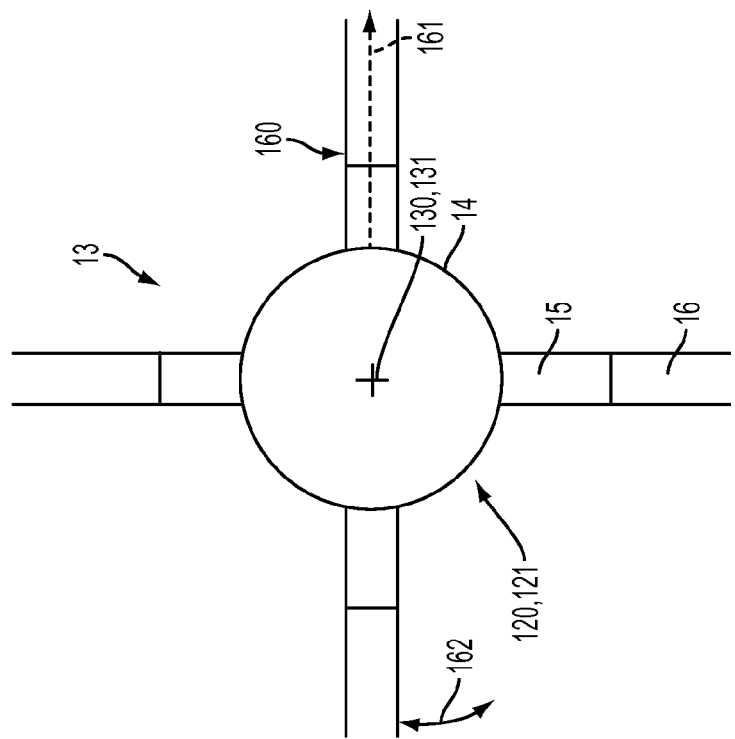
FIG. 2 is an enlarged view of a portion of a main rotor of the aircraft of FIG. 1.

With reference to FIGS. 1 and 2, an aircraft 10 is provided and may be a helicopter 11 or another similar type of aircraft. The helicopter 11 includes a non-rotational frame (i.e., an airframe) 12 and rotational frames 13. One or more of the rotational frames 13 may be provided on a top portion of the non-rotational frame 12 as a main rotor 120 and another may be provided at a rear of the non-rotational frame 12 as a tail rotor 121. An engine and a transmission are contained within the non-rotational frame 12 to drive rotation of the rotational frames 13 about rotational axes 130 and 131 with respect the non-rotational frame 12. Such rotation of the main rotor 120 provides for lift and thrust of the helicopter 11 and rotation of the tail rotor 121 provides for attitude control of the helicopter.

While the aircraft 10 is shown as a coaxial aircraft, it is understood that aspects can be used in non-coaxial aircraft or other types of coaxial aircraft having other configurations.

The main rotor 120 rotates about rotational axis 130 and includes a hub 14 through which the rotational axis 130 is defined, a plurality of hub-arms 15 and a plurality of blades 16. Each blade 16 extends radially outwardly from the hub 14 and includes an inner radial portion 160 that is coupled to the hub 14 by way of an associated one of the hub arms 15. During flight, the blades 16 can be controlled cyclically or collectively to pitch around pitch axes 161 that are defined along longitudinal lengths of each of the blades 16. However, in practice, each of the blades 16 may tend to pitch around the corresponding pitch axis 161 more or less than desired and additionally may exhibit lead/lag errors in the circumferential dimension 162 as well as flapping errors in the height-wise dimension 163.

With reference to FIGS. 1 and 3-5, the helicopter 11 may further include a flight computer 20, a rotor state sensor system 25 and a transmission system 26. The flight computer 20 is supportively disposed in the non-rotational frame 12. The flight computer 20 controls the driving of the main rotor 120 and the tail rotor 121 as well as the cyclic and collective control of the blades 16. The flight computer 20 is responsive to pilot commands and flight control algorithms some of which will be described below. The rotor state sensor system 25 is provided at least partially in the rotational frame 12 and may be communicative with the flight computer 20 by way of the transmission system 26 such that the flight computer 20 can be receptive of information or signals from the rotor state sensor system 25. The received information or signals can be employed by the flight computer 20 to alter or govern the flight control algorithms. The transmission system 26 can be a wired and/or wireless data transmission system.

Figure 4:
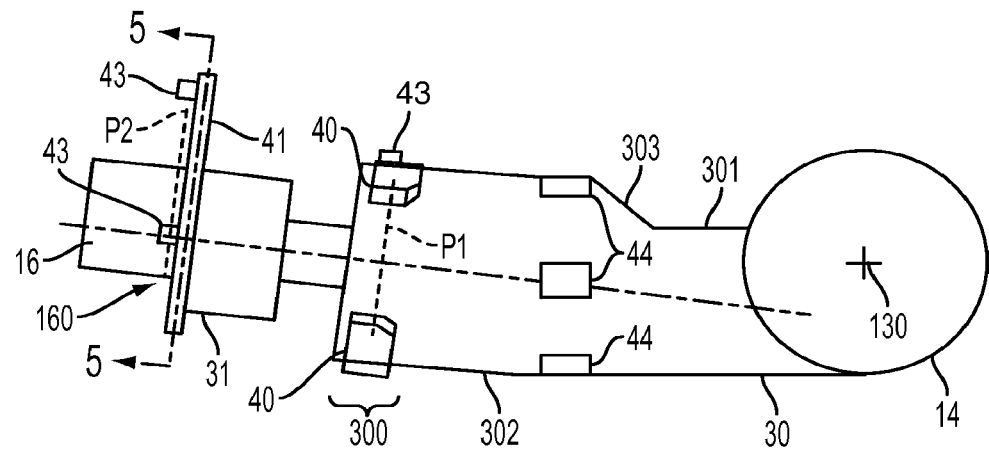
FIG. 4 is a plan view of components of the main rotor of the aircraft of FIG. 1 in accordance with embodiments.

A connection between a single blade 16 and the hub 14 includes a single hub arm 30 and a connector element 31. The hub arm 30 extends radially outwardly from the hub 14 and the connector element 31 serves to couple the inner radial portion 160 of the blade 16 with an outer radial portion 300 of the hub arm 30. As shown in FIG. 4, the hub arm 30 may include a narrow portion 301 that is proximate to the hub 14, a wide portion 302 that extends out toward the outer radial portion 300 and a tapered portion 303 that connects the narrow portion 301 to the wide portion 302. The connector element 31 may include a spindle element, an elastomeric bearing or an inner nut of an elastomeric bearing. However, it is understood that the hub arm 30 can have other shapes and configurations in other aspects of the invention.

In accordance with embodiments, the rotor state sensor system 25 may include a plurality of sensors 40 and a plurality of reflectors 41. Each sensor 40 is mounted on or near the outer radial portion 300 of the hub arm 30 and each reflector plate 41 is mounted on or near the inner radial portion 160 of the blade 16. Each of the sensors 40 can be configured to provide and issue a first signal S1 (see FIG. 3) that is indicative of a position of the sensor 40 on the hub arm 30, or such positions can be programmed. The sensors 40 also each generate an emission directed toward an associated one of the reflector plates 41. The locations on each of the reflector plates 41 (such as the distance and/or angles relative to the sensors 40) where the corresponding emissions are incident are detectable or determinable by the sensor 40 and/or by additional sensors in accordance with a direction of reflection of the emissions. Alternatively, the distances between the respective positions of the sensors 40 and the respective positions of the incident locations of the reflector plates 41 are detectable or determinable by the sensor 40 or by the additional sensors.

In any case, with the incident locations known, each of the sensors 40 is further configured to provide and issue a second signal S2 (see FIG. 3) that is indicative of respective positions of the incident locations of the reflector plates 41. The combined first signals of the sensors 40 define a first plane P1 at or near the outer radial portion 300 of the hub arm 30 and the combined second signals define a second plane P2 at or near the inner radial portion 160 of the blade 16.

Figure 3:
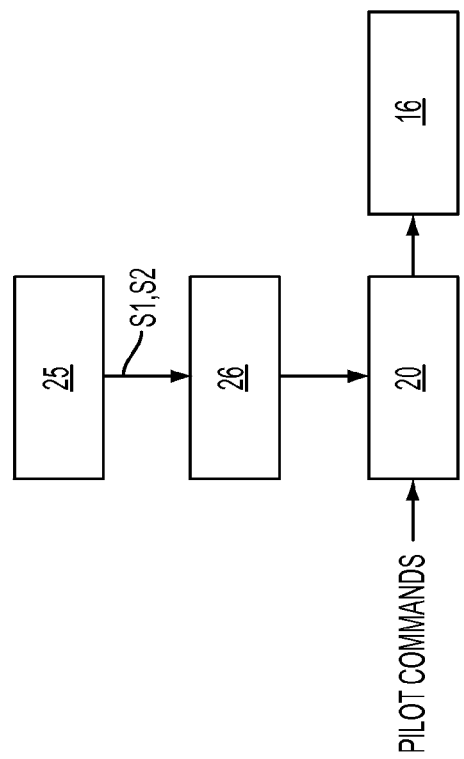
FIG. 3 is a schematic diagram of a flight computer of the aircraft of FIG. 1 in accordance with embodiments.

As shown in FIG. 3, the first and second signals S1 and S2 may be transmitted from the sensors 40 to the flight computer 20 by way of the transmission system 26. The transmission system 26 may include transmitters coupled to the sensors 40 and disposed in the rotational frame 12 and receivers coupled to the flight computer 20 and disposed in the non-rotational frame 13. The transmitters may be components of the sensors 40 and the receivers may be components of the flight computer 20.

Figure 6:
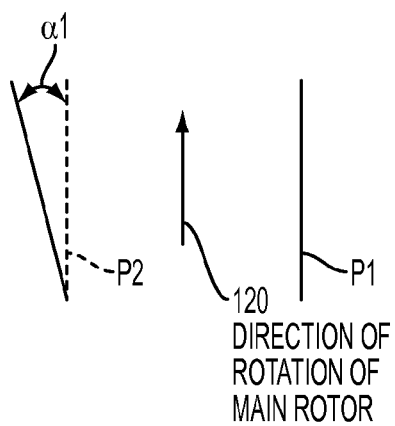
FIG. 6 is a schematic diagram of a first angle formed between first and second planes.
Figure 7:
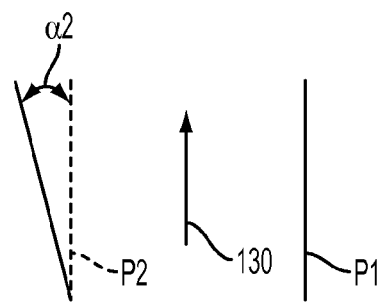
FIG. 7 is a schematic diagram of a second angle formed between first and second planes.

With the first and second signals S1 and S2 transmitted to the flight computer 20 by way of the transmission system 26, the flight computer 20 is configured to recognize the first and second planes P1 and P2 and their respective orientations and to ascertain from such recognition the relative orientations of the first and second planes P1 and P2 with respect to one another. With reference to FIGS. 6 and 7 and, from the relative orientations of the first and second plane P1 and P2, a lead/lag condition of the blade 16 can be identified (see FIG. 6) in accordance with an angle $\alpha 1$ defined by the first and second planes P1 and P2 in the plane of the main rotor 120 and a flapping condition of the blade 16 can be identified (see FIG. 7) in accordance with an angle $\alpha 2$ defined by the first and second planes P1 and P2 relative to the rotational axis 130.

As an example, an operation of the plurality of sensors 40 and the plurality of reflectors 41 in accordance with embodiments will now be explained. The plurality of sensors 40 includes sensor 1, sensor 2 and sensor 3 whose measurements are d1, d2 and d3, respectively, and whose sensor points are as follows.

$$s_p1=[0,y1,z1]^T$$

$$s_p2=[0,y2,z2]^T$$

$$s_p3=[0,y3,z3]^T$$

The plurality of reflectors 41 includes reflector 1, reflector 2 and reflector 3, whose reflector points are as follows.

$$r_p1=[d1,y1,z1]^T$$

$$r_p2=[d2,y2,z2]^T$$

$$r_p3=[d3,y3,z3]^T$$

The next step is to determine a vector normal to the first plane P1 ($s_{normal}$) and normal to the second plane P2 ($r_{normal}$). Since the first plane P1 is aligned with the coordinate axis, the vector normal to the first plane P1 is assumed to be $s_{normal}=[1, 0, 0]^T$. The cross-products between two vectors in the second plane P2 are used to determine the reflector normal vector, $r_{normal}$.

$$r_{normal}=(r_p1-r_p2)\times(r_p1-r_p3)$$

The flapping angle β and lead-lag angle ζ are determined by the angles of $r_{normal}$ relative to $s_{normal}$. To determine β, the reflector normal vector $r_{normal}$ is projected into the x-z-plane, and to determine, the $r_{normal}$ is projected into the x-y-plane. The equations for β and ζ are as follows.

$$\beta=\tan^{-1}(r_{normal}(3)/r_{normal}(1))$$

$$\zeta=\tan^{-1}(r_{normal}(2)/r_{normal}(1))$$

It should also be noted that when a hub already has "pre-cone" and "pre-lag" (also known as "thrust offset"), that should be added to the flapping and lead-lag values. Also, the distance between the P1 and P2 planes ($d_{s\rightarrow r}$) can be determined from the average of the sensor readings as follows:

$$d_{s\rightarrow r}=\Sigma(\text{from } i=0 \text{ to } N_s)d_i=(d_1+d_2+d_3)/3$$

where i is the sensor index, $N_s$ is the number of sensors and $d_i$ is the distance measurement for sensor i. In order to determine the extension of the thrust bearing $d_{ext}$, the nominal distance $d_{nom}$ between planes P1 and P2 would need to be subtracted from $d_{s\rightarrow r}$.

$$d_{ext}=d_{s\rightarrow r}-d_{nom}.$$

In accordance with embodiments, the mounting of the sensors 40 on or near the outer radial portion 300 of the hub arm 30 and then mounting of the reflector plates 41 on or near the inner radial portion 160 of the blade 16 (i.e., the root of the blade 16) allows for accuracy in the measurements of the lead/lag and the flapping conditions. That is, the measurements of the conditions include little to no effects of high-order blade bending and torsional deflection due to the reflector plates 41 being located at the blade 16 root, for example.

Figure 5:
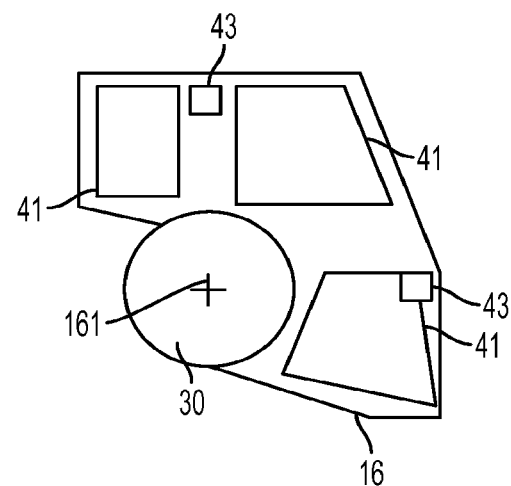
FIG. 5 is a radial view taken along line A-A in FIG. 4.

As shown in FIGS. 4 and 5 and, in accordance with further embodiments, rotor state sensor system 25 may further include accelerometers 43 and strain gages 44. The accelerometers 43 may be disposed proximate to each of the sensors 40 and each of the reflector plates 41 and can generate measurement results indicative of first order motion of the blade 16 relative to the hub arm 30 that can serve as a steady reference point for comparison with and verification of the sensor 40 measurements. The strain gages 44 may be disposed proximate to the tapered portion 303 of the hub arm 30 such that strain may be measured on the hub arm 30 inboard of the sensors 40. Strain in the hub arm 30 may be proportional to blade 16 lagging and should be correlated with the sensor 40 measurements.

Figure 8:
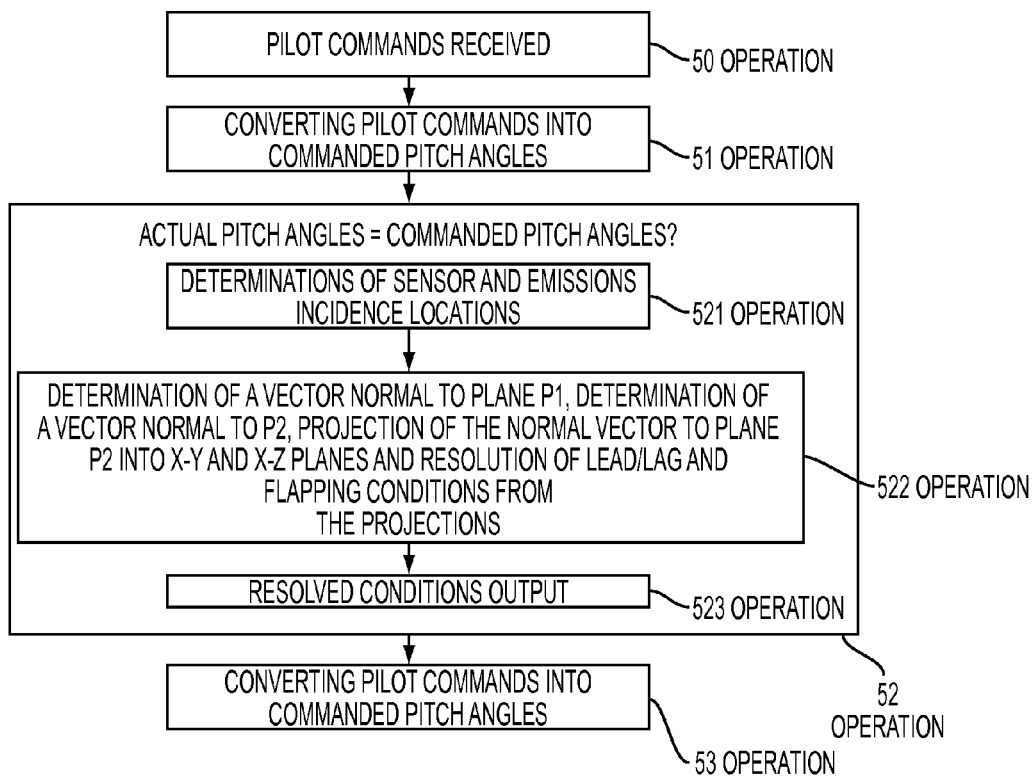
FIG. 8 is a flow diagram illustrating a method of controlling an aircraft in accordance with embodiments.

With reference to FIG. 8, a method of controlling the aircraft 10 will now be described. As shown in FIG. 8, pilot commands (i.e., cyclic and collective commands) are received by the flight computer 20 in operation 50 and those commands are converted into commanded pitch angles for each of the blades 16 in operation 51. At this point, the rotor state sensor system 25 is engaged to determine whether the actual pitch angles for the blades 16 are in-line with the commanded pitch angles in operation 52. In an event the actual pitch angles are different from the commanded pitch angles by a predefined degree, the flight computer 20 readjusts the commanded pitch angles in operation 53 to refine the pitch of the blades 16.

In accordance with further embodiments and, as shown in FIG. 8, operation 52 may include a determination of sensor 40 positions and an additional determination of distances between the sensors 40 and the positions of the corresponding emissions incidence locations at operation 521. Operation 52 may further include, at operation 522, a determination of a vector normal to plane P1, a determination of a vector normal to P2, a projection of the normal vector to plane P2 into x-y and x-z planes and a resolution of lead/lag and flapping conditions from the projections. Operation 52 is completed with the resolved lead/lag and flapping conditions being output at operation 523 and, for example, used by the flight computer 20 to adjust the commanded pitch angles for the blades 16 in operation 53.

While the invention has been described in detail in connection with only a limited number of embodiments, it should be readily understood that the invention is not limited to such disclosed embodiments. Rather, the invention can be modified to incorporate any number of variations, alterations, substitutions or equivalent arrangements not heretofore described, but which are commensurate with the spirit and scope of the invention. By way of example, aspects can be used on fixed wing aircraft, wind turbine blade control, maritime blade control, or any other implementation where blade position needs to be accurately assessed. Additionally, while various embodiments of the invention have been described, it is to be understood that aspects of the invention may include only some of the described embodiments. Accordingly, the invention is not to be seen as limited by the foregoing description, but is only limited by the scope of the appended claims.

What is claimed is:

1. A rotor state sensor system for use with a rotor including a hub, a hub arm and a blade coupled to the hub by the hub arm, the sensor system comprising:
   a plurality of sensors disposed on a radially outer portion of the hub arm to define a first plane, which emit emissions and receive reflected emissions, and which generate a signal according to the received reflected emissions;
   a plurality of reflector plates disposed at varying positions about a pitch axis of the blade on a radially inward portion of the blade and which define a second plane at locations where the emissions from the sensors are incident on the reflector plates and from which the reflected emissions are reflected towards the sensors
   the sensors being configured to detect the locations from the reflected emissions and to generate the signal to be indicative of the locations; and a computing device which receives the signal from the sensors, determines relative orientations of the first and second planes according to the received signal and determines a condition of the rotor based on the determined relative orientations.

2. The rotor state sensor system according to claim 1, further comprising a transmission system by which signals are transmittable between the sensors and the computing device.

3. The rotor state sensor system according to claim 1, wherein the condition comprises at least one or more of a lead/lag condition and a flapping condition.

4. The rotor state sensor system according to claim 1, the rotor state sensor system integrated with a helicopter, the helicopter comprising:
 a non-rotating frame in which the computing device is disposed; and
 a rotating frame comprising the rotor, sensors and reflector plates,
 wherein the computing device is further configured to adjust commanded pitch angles in accordance with the signals.

5. A rotor state sensor system, comprising:
 a rotor including a hub, a hub arm and a blade coupled to the hub by the hub arm;
 a plurality of sensors disposed on a radially outer portion of the hub arm to define a first plane;
 a plurality of reflector plates disposed at varying positions about a pitch axis of the blade on a radially inward portion of the blade such that emissions generated by the sensors define a second plane at locations where the emissions are incident on the reflector plates,
 the plurality of sensors being configured to detect the locations from reflected emissions of the plurality of reflector plates and to generate a first signal indicative of the first plane and a second signal indicative of the locations; and
 a computing device receptive of the and second signals from the sensors, and,
 with the first and second signals being indicative of relative orientations of the first and second planes with respect to one another, the computing device is configured to determine at least one or more of a lead/lag condition and a flapping of the rotor based on the first and second signals.

6. The rotor state sensor system according to claim 5, further comprising a transmission system by which the first and second signals are transmittable between the sensors and the computing device.

7. The rotor state sensor system according to claim 1, the rotor state sensor system integrated with a helicopter, the helicopter comprising:
 a non-rotating frame in which the computing device is disposed; and
 a rotating frame comprising the rotor, sensors and reflector plates, with the reflector plates being disposed on a radially inward portion of the blade,
 wherein the computing device is further configured to adjust commanded pitch angles in accordance with the signals.

8. The rotor state sensor system according to claim 1, wherein the computing device determines:
 respective vectors normal to the first and second planes,
 a flapping angle of the hub arm and the blade as a relative angle in an x- and z-plane of the respective vectors normal to the first and second planes, and
 a lead-lag angle of the hub arm and the blade as a relative angle in an x- and y-plane of the respective vectors normal to the first and second planes.

9. The rotor state sensor system according to claim 8, wherein the computing device accounts for pre-cone and pre-lag of the hub in determining the flapping and lead-lag angles.

* * * * *